US00PP20091P2

(12) United States Plant Patent
Hartman

(10) Patent No.: US PP20,091 P2
(45) Date of Patent: Jun. 9, 2009

(54) ***CALADIUM* PLANT NAMED 'STARBURST'**

(50) Latin Name: ***Caladium* × *hortulanum***
Varietal Denomination: Starburst

(76) Inventor: Robert Dale Hartman, 158 Blue Moon Ave., Lake Placid, FL (US) 33852

( * ) Notice: Subject to any disclaimer, the term of this patent is extended or adjusted under 35 U.S.C. 154(b) by 0 days.

(21) Appl. No.: 12/070,570

(22) Filed: Feb. 19, 2008

(51) Int. Cl.
*A01H 5/00* (2006.01)

(52) U.S. Cl. ..... Plt./373

(58) Field of Classification Search ..... Plt./373
See application file for complete search history.

*Primary Examiner*—June Hwu
(74) *Attorney, Agent, or Firm*—C. A. Whealy

(57) ABSTRACT

A new and distinct cultivar of *Caladium* plant named 'Starburst', characterized by its compact plant habit; vigorous and dense growth habit; and strap-type leaves that are red purple in color in the center with green-colored borders and dark green-colored margins; when mature, veins are whitish giving a star-like appearance.

5 Drawing Sheets

Botanical designation: *Caladium×hortulanum.*
Cultivar denomination: 'Starburst'.

BACKGROUND OF THE INVENTION

The present invention relates to a new and distinct cultivar of *Caladium* plant, botanically known as *Caladium× hortulanum* commercially referred to as a strap leaf-type *Caladium* and hereinafter referred to by the name 'Starburst'.

The objective of the Inventor's breeding program is to create new *Caladium* cultivars that have uniform plant habit, exceptional performance and attractive foliage coloration.

The new *Caladium* originated from a cross-pollination made by the Inventor in June, 2001, in Lake Placid, Fla. of the *Caladium×hortulanum* cultivar White Wing, not patented, as the female, or seed, parent with the *Caladium× hortulanum* cultivar Freida Hemple, not patented, as the male, or pollen, parent. The new *Caladium* was discovered and selected by the Inventor as a single plant within the progeny of the stated cross-pollination in a controlled environment in Lake Placid, Fla. on May 15, 2002.

Asexual reproduction of the new cultivar by tuber divisions in a controlled environment in Lake Placid, Fla. since Apr. 15, 2003 has shown that the unique features of this new *Caladium* are stable and reproduced true to type in successive generations of asexual reproduction.

SUMMARY OF THE INVENTION

The cultivar Starburst has not been observed under all possible environmental conditions. The phenotype may vary somewhat with variations in environment such as temperature and light intensity, without, however, any variance in genotype.

The following traits have been repeatedly observed and are determined to be the unique characteristics of 'Starburst'. These characteristics in combination distinguish 'Starburst' as a new and distinct cultivar of *Caladium:*

1. Compact plant habit.
2. Vigorous and dense growth habit.

3. Strap-type leaves that are red purple in color in the center with green-colored borders and dark green-colored margins; when mature, veins are whitish giving a star-like appearance.

Plants of the new *Caladium* differ from plants of the female parent, the cultivar White Wing, in the following characteristics:

1. Plants of the new *Caladium* are more compact than and not as upright as plants of the cultivar White Wing.
2. Leaves of plants of the new *Caladium* are more oval in shape than leaves of plants of the cultivar White Wing.
3. Plants of the new *Caladium* and the cultivar White Wing differ in leaf coloration as plants of the cultivar White Wing have white-colored leaves with mottled dark and light green-colored borders.

Plants of the new *Caladium* differ from plants of the male parent, the cultivar Freida Hemple, in the following characteristics:

1. Plants of the new *Caladium* are more compact than and not as upright as plants of the cultivar Freida Hemple.
2. Leaves of plants of the new *Caladium* are not as rounded in shape as leaves of plants of the cultivar Freida Hemple.
3. Plants of the new *Caladium* and the cultivar Freida Hemple differ in leaf coloration as plants of the cultivar Freida Hemple have bright red-colored leaves with dark green-colored borders.

Plants of the new *Caladium* can also be compared to plants of the cultivar Florida Sweetheart, disclosed in U.S. Plant Pat. No. 8,526. In side-by-side comparisons conducted in Lake Placid, Fla., plants of the new *Caladium* differed primarily from plants of the cultivar Florida Sweetheart in leaf coloration as plants of the cultivar Florida Sweetheart had leaves that are light pink in color in the center with dark green-colored margins and pink-colored venation.

BRIEF DESCRIPTION OF THE PHOTOGRAPHS

The accompanying photographs illustrate the overall appearance of the new *Caladium.* These photographs show the colors as true as it is reasonably possible to obtain in colored reproductions of this type. Colors in the photographs may differ slightly from the color values cited in the detailed botanical description which accurately describe the colors of the new *Caladium*.

The photograph on the first sheet is a side perspective view of a typical plant of 'Starburst' grown in a container in a shadehouse.

The photograph at the top of the second sheet is a side perspective view of typical plants of 'White Wing' (left), 'Starburst' (center) and 'Freida Hemple' (right) grown in a shadehouse.

The photograph at the bottom of the second sheet is a side perspective view of typical plants of 'Florida Sweetheart' (left) and 'Starburst' (right) grown in a shadehouse.

The photograph at the top of the third sheet is a side perspective view of typical plants of 'Starburst' grown in an outdoor nursery.

The photograph at the bottom of the third sheet is a close-up view of typical leaf petioles, tubers and roots of 'Starburst'.

The photograph on the fourth sheet is a side perspective view of an individual plants grown in an outdoor nursery.

The photograph on the fifth sheet is a close-up view of the upper surface of a typical leaf from a plant grown in an outdoor nursery.

DETAILED BOTANICAL DESCRIPTION

In the following description, color references are made to The Royal Horticultural Society Colour Chart, 2001 Edition, except where general terms of ordinary dictionary significance are used. The aforementioned photographs and following observations and measurements describe plants grown in 15-cm containers in Avon Park, Fla. during the summer in a polypropylene-covered shadehouse and plants grown in ground beds in Zolfo Springs, Fla. during the late summer in an outdoor nursery. All plants were grown under conditions and practices which approximate those generally used in commercial *Caladium* production. During the production of the plants, day temperatures ranged from about 20° C. to 30° C., night temperatures ranged from about 10° C. to 20° C. and light levels were about 8,000 foot-candles (shadehouse) or 10,000 to 12,000 foot-candles (outdoor nursery). Plants grown in the shadehouse were about seven weeks from planting tubers when the photographs and the detailed description were taken. Plants grown in the outdoor nursery were about four months from planting tuber pieces when the photographs and the detailed description were taken.

Botanical classification: *Caladium×hortulanum* cultivar Starburst.

Parentage:

*Female, or seed, parent.*—*Caladium×hortulanum* cultivar White Wing, not patented.

*Male, or pollen, parent.*—*Caladium×hortulanum* cultivar Freida Hemple, not patented.

Propagation:

*Type.*—By tubers and by tuber divisions.

*Time to initiate roots, summer.*—About seven to ten days at 32° C.

*Time to initiate roots, winter.*—About two to three weeks at 24° C.

*Tuber description.*—Number of buds per tuber, shadehouse-grown plants: About 15 actively growing buds/shoots. Number of buds per tuber, outdoor nursery-grown plants: About four actively growing buds/shoots. Height: About 2.5 cm. Diameter: About 3.7 cm. Texture: Thick, starchy; somewhat brittle. Color: Epidermis, between 165C to 165D; interior, 4C to 4D. Root description: Dense, thick and white fleshy roots.

Plant description:

*Plant type.*—Herbaceous perennial.

*Plant/growth habit.*—Compact and upright plant habit; inverted triangle. Vigorous, dense growth habit; suitable for 10-cm to 25-cm containers. Leaf petioles arising from tubers; petioles mostly upright and curving outwardly with development.

*Plant height, from soil level to top of leaf plane, shadehouse-grown plants.*—About 28 cm.

*Plant height, from soil level to top of inflorescences, shadehouse-grown plants.*—About 31 cm.

*Plant diameter or spread, shadehouse-grown plants.*—About 41 cm.

*Plant height, from soil level to top of leaf plane, outdoor nursery-grown plants.*—About 30 cm to 35 cm.

*Plant height, from soil level to top of inflorescences, outdoor nursery-grown plants.*—Inflorescences not observed on plants grown in the outdoor nursery.

*Plant diameter or spread, outdoor nursery-grown plants.*—About 50 cm.

*Cataphylls* (*only observed on shadehouse-grown plants*).—Length: About 8 cm. Width: About 1.4 cm. Shape: Linear. Apex: Acute to cuspidate. Base: Sheathing the stem. Color, inner and outer surfaces: Between 182D and 156A variably streaked with N186C; with development, color becoming closer to 200A to 200B.

Foliage description:

*Length, shadehouse-grown plants.*—About 15.5 cm to 18 cm.

*Width, shadehouse-grown plants* (*flattened*).—About 11 cm to 14 cm.

*Length, outdoor nursery-grown plants.*—About 17 cm to 22 cm.

*Width, outdoor nursery-grown plants* (*flattened*).—About 11 cm to 14 cm.

*Shape.*—Ovate.

*Apex.*—Acuminate to acute.

*Base.*—Sagittate to cordate.

*Margin.*—Entire; undulate.

*Texture, upper surface.*—Smooth, glabrous.

*Texture, lower surface.*—Smooth, glabrous; glaucous.

*Venation pattern.*—Pinnate.

*Color, shadehouse-grown plants.*—Developing and fully expanded leaves, upper surface: Center: 53C. Border and margins: 147A and random streaks of 183A, 137A and 194B to 194C; basal notch, 53C. Venation: Midrib and primary veins, 53C to 53D; color becoming closer to 145C to 145D with development. Developing and fully expanded leaves, lower surface: Center: 63B to 63C. Border and margins: 147B and random streaks of 63B to 63C and 59D. Venation: Midrib, 195B and 182D; primary veins, 160D and 195B.

*Color, outdoor nursery-grown plants.*—Developing leaves, upper surface: Center: Variable areas of 63A and 60A. Border and margins: Random areas and streaks of 137A, 146D, 145D and 147A. Venation: Midrib and primary veins, 145C to 145D variably tinged with 63A to 63B. Developing leaves, lower surface: Center: 63A to 63B. Border and margins: Random areas and streaks of 147D and 144C to 144D; at the margins, 147B to 147C. Venation: Midrib and primary veins, between 145D and 147D. Fully expanded leaves, upper surface: Center: Variable areas of 63A, 53A to 53C, 60A and 183A. Border and margins: Random areas and streaks of 145C, 146D, 137A and 147A. Venation: Midrib, between 147D and 145C variably streaked with 60A, distally flushed with 60A; primary veins, between 147D and 145C variably streaked with 60A. Fully expanded leaves, lower surface: Center: Between 63A to 63B and 59D. Border and margins: 147B. Venation: Midrib, between 147D and 146D; primary veins, 147C.

*Petiole.*—Aspect: Mostly erect, curving outwardly with development. Length, shadehouse-grown plants: About 21 to 26 cm. Diameter, distal, shadehouse-grown plants: About 4.5 mm. Diameter, proximal, shadehouse-grown plants: About 7 mm. Length, outdoor nursery-grown plants: About 28 cm to 32 cm. Diameter, distal, outdoor nursery-grown plants: About 4.5 mm. Diameter, proximal, outdoor nursery-grown plants: About 6 mm. Strength: Strong; flexible. Color, shadehouse-grown plants: Between 182C to 182D and 156C variably streaked with between N186C and 200A. Color, proximal, outdoor nursery-grown plants: 147B densely streaked with N186C. Wing length, shadehouse-grown plants: About 7 cm to 9 cm. Wing diameter, shadehouse-grown plants: About 7.5 mm to 9 mm. Wing length, outdoor nursery-grown plants: About 9 cm. Wing diameter, outdoor nursery-grown plants: About 9 mm. Wing color, shadehouse-grown plants: Between 182C to 182D and 156A streaked with N186C. Wing color, outdoor nursery-grown plants: 147C streaked with N186C.

Inflorescence description: Inflorescences only observed on shadehouse-grown plants.

*Inflorescence arrangement.*—Upright hooded spathes surrounding a columnar spadix borne on a tall upright scape. Spadix with sessile, simple female and male flowers separated into two zones. Female flowers arranged on the lower one-third of the spadix; male flowers arranged on the upper two-thirds of the spadix. Sterile flowers develop between female and male flower zones; near this area, the spathe constricts surrounding the female flowers.

*Fragrance.*—None detected.

*Natural flowering season/longevity.*—Plants of the new *Caladium* typically flower during the spring or early summer in central Florida. Flowers develop about seven weeks after growth commences. Inflorescences last about three days before fading; inflorescences persistent.

*Spathe.*—Length: About 15 cm. Width, distal: About 5 cm. Width, proximal: About 2.7 cm. Shape: Ovate to somewhat obovate. Apex: Acute to acuminate. Base: Tapering. Margin: Entire; proximal, notched. Texture, upper and lower surfaces: Smooth, glabrous. Color: Front surface: Upper two-thirds: 157C. Color becoming closer to more brown than 199D with development. Lower one-third: 147C to 147D. Rear surface: Upper two-thirds: Between 145D and 146D. Lower one-third: 147C streaked with 147B. Spadix: Length, entire spadix: About 8.5 cm. Length, male flower zone: About 5.7 cm. Length, sterile flower zone: About 1.9 cm. Length, female flower zone: About 1.3 cm. Diameter, male flower zone: About 1.1 cm. Diameter, sterile flower zone: About 1 cm. Diameter, female flower zone: About 8 mm. Shape: Spindle-shaped to columnar. Apex: Obtuse. Base: Obtuse. Aspect: Upright. Color, mature, male zone: 158A. Color, mature, sterile zone: 158A Color, mature, female zone: 9C. Male flowers: Quantity per spadix: About 260. Shape: Obovate. Height: About 3 mm. Diameter: About 3 mm. Anther color: Close to 157D. Amount of pollen: None observed. Female flowers: Quantity per spadix: About 70. Shape: Obovate. Height: About 3 mm. Diameter: About 2 Mm. Stigma color: 9C. Ovary color: 155D. Scape: Length: About 21 cm. Diameter: About 6.5 mm. Strength: Sturdy; flexible. Aspect: Erect. Texture: Smooth, glabrous; glaucous. Color: 182B to 182C densely streaked with between N186C and 200A; just below spathe, 148B to 148C. Seed and fruit: Seed and fruit development has not been observed on plants of the new *Caladium.*

Disease/pest resistance: Plants of the new *Caladium* have been observed to be somewhat tolerant to *Pythium* root rot and *Xanthomonas* leaf spot. Plants of the new *Caladium* have not been observed to be resistant to pests or other pathogens common to *Caladium.*

Temperature tolerance: Plants of the new *Caladium* have been observed to be tolerant to temperatures ranging from about 7° C. to about 40° C.

It is claimed:

1. A new and distinct *Caladium* plant named 'Starburst' as illustrated and described.

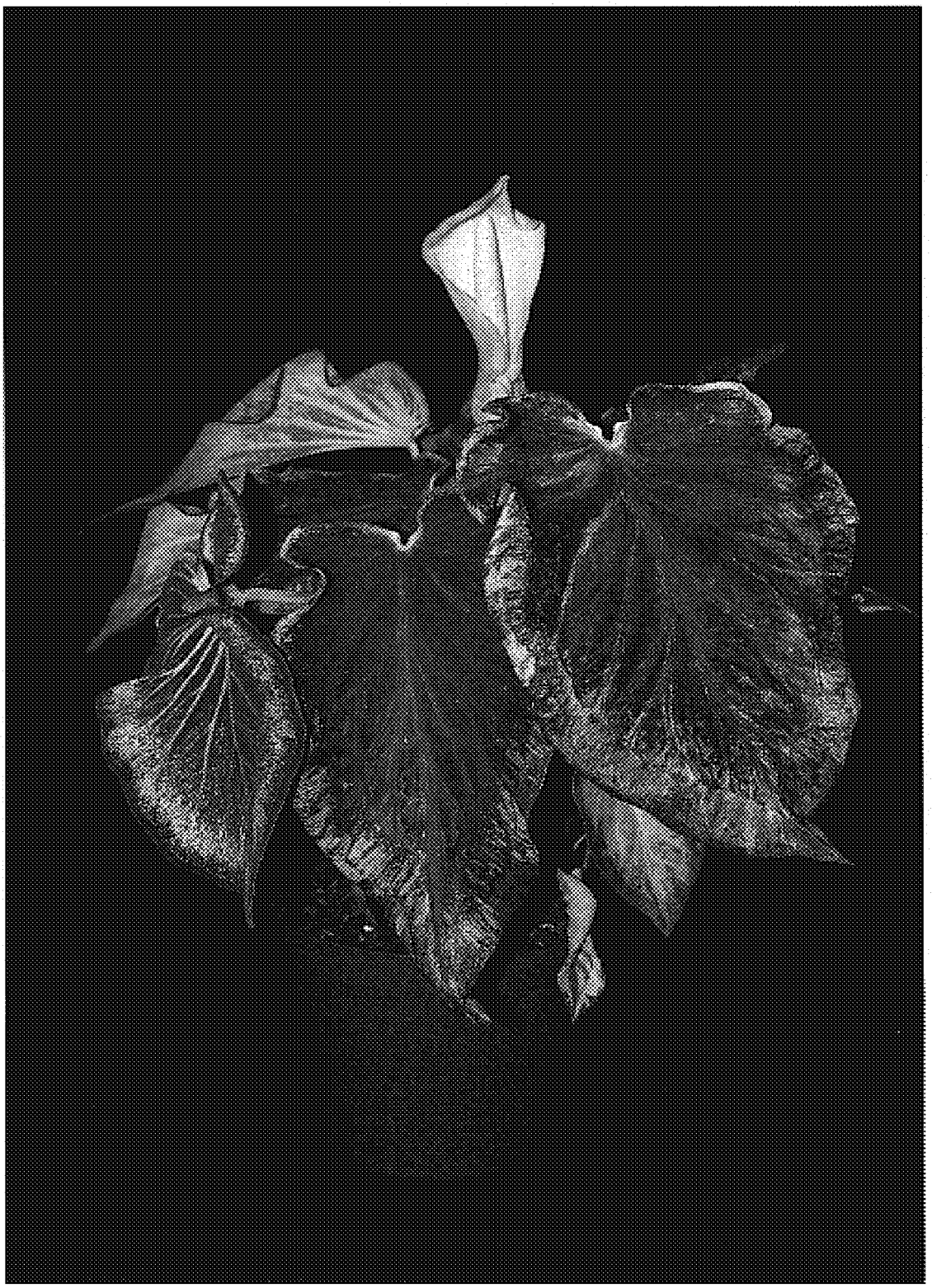

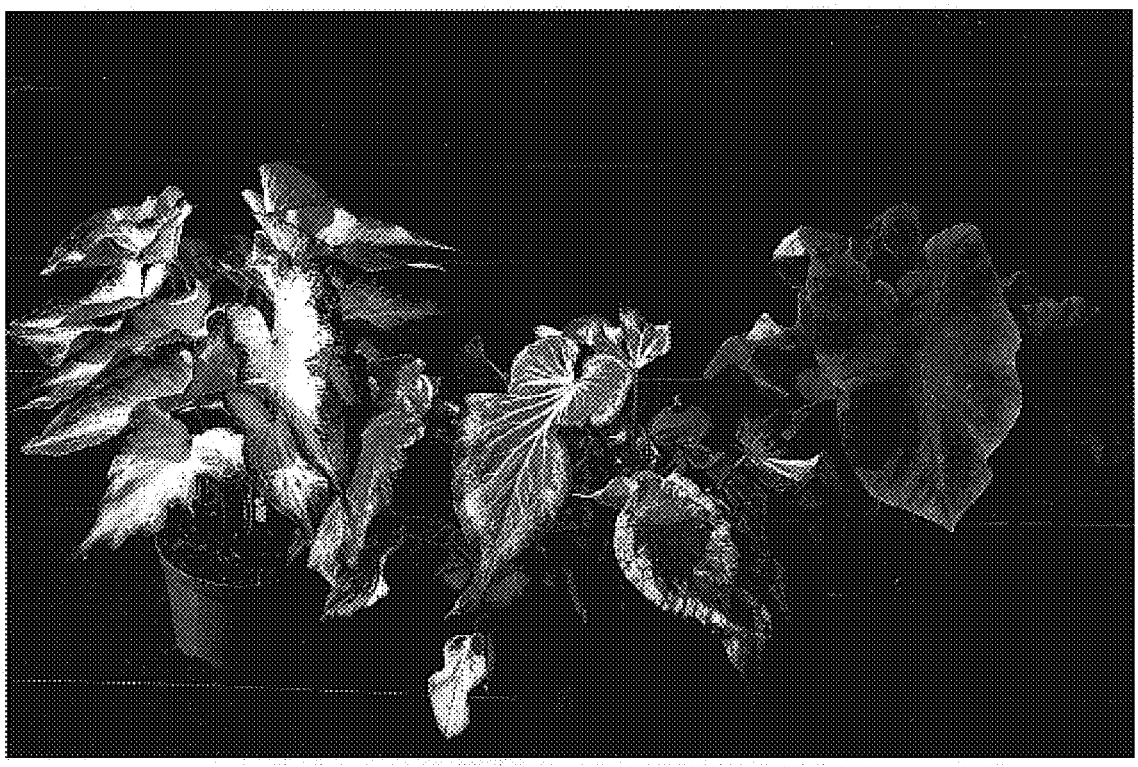
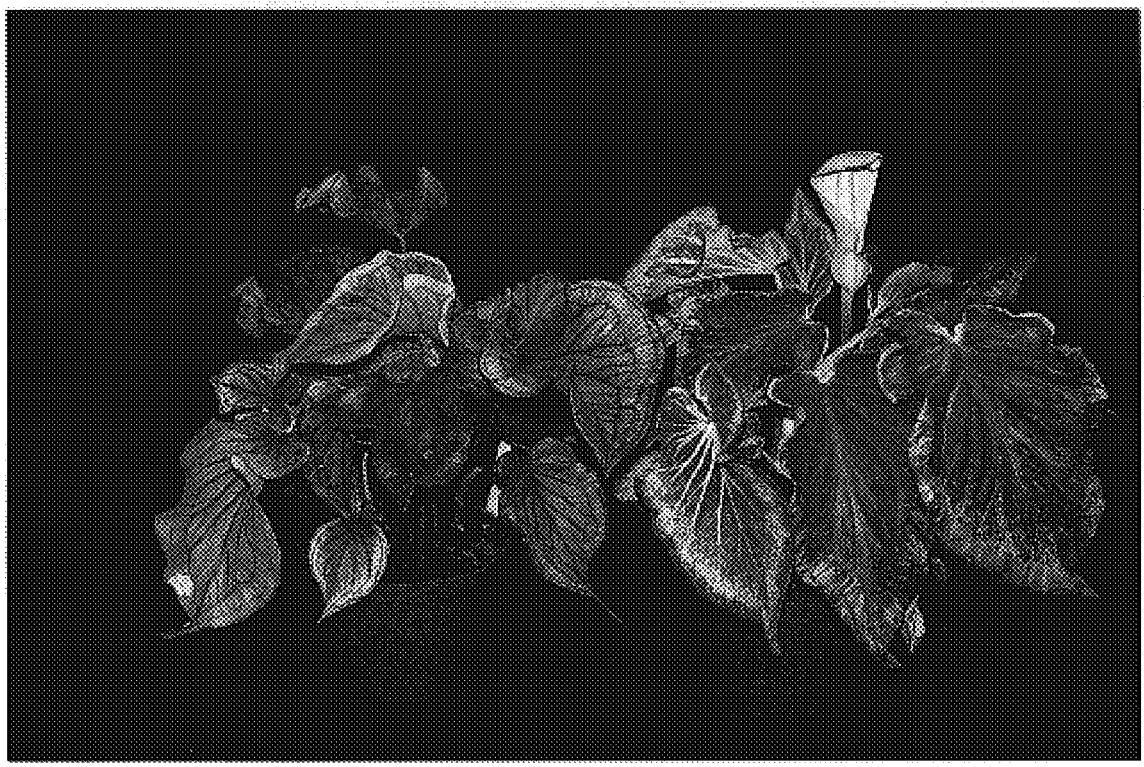

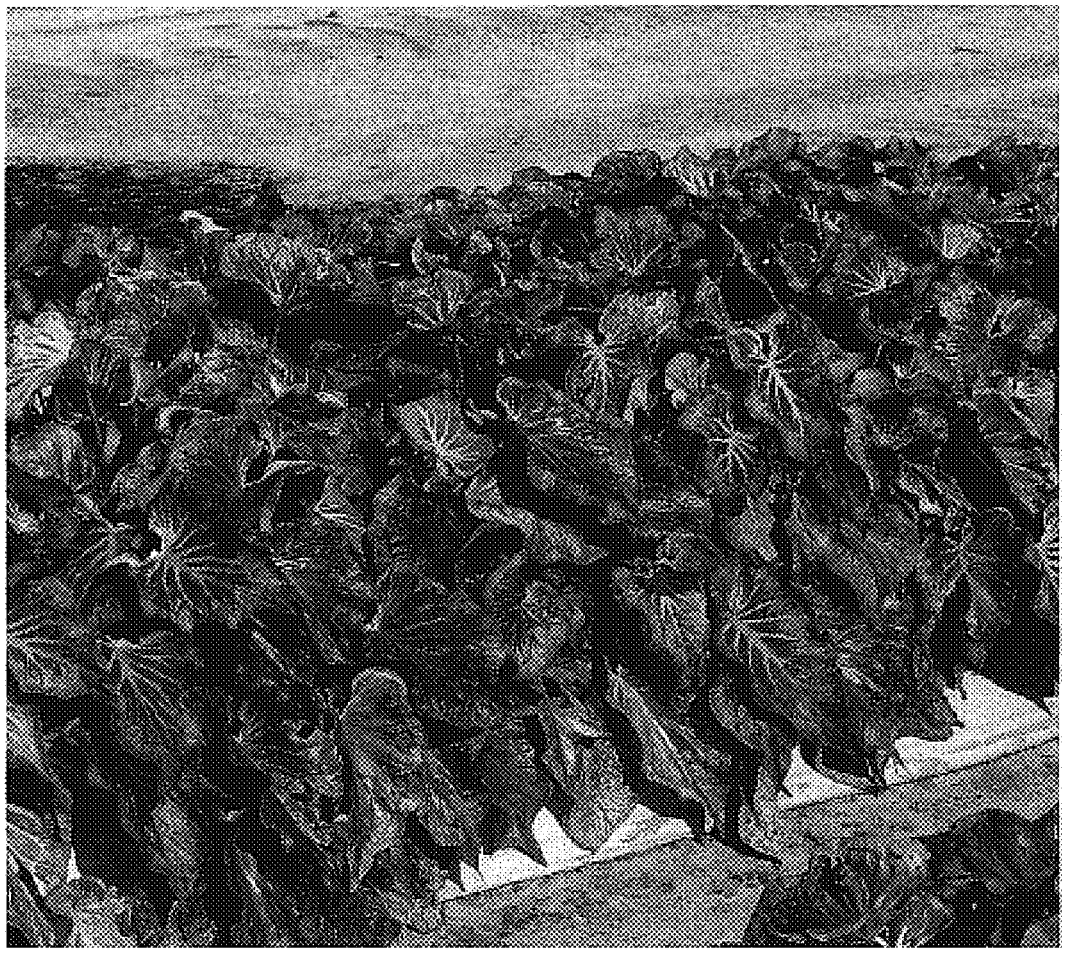
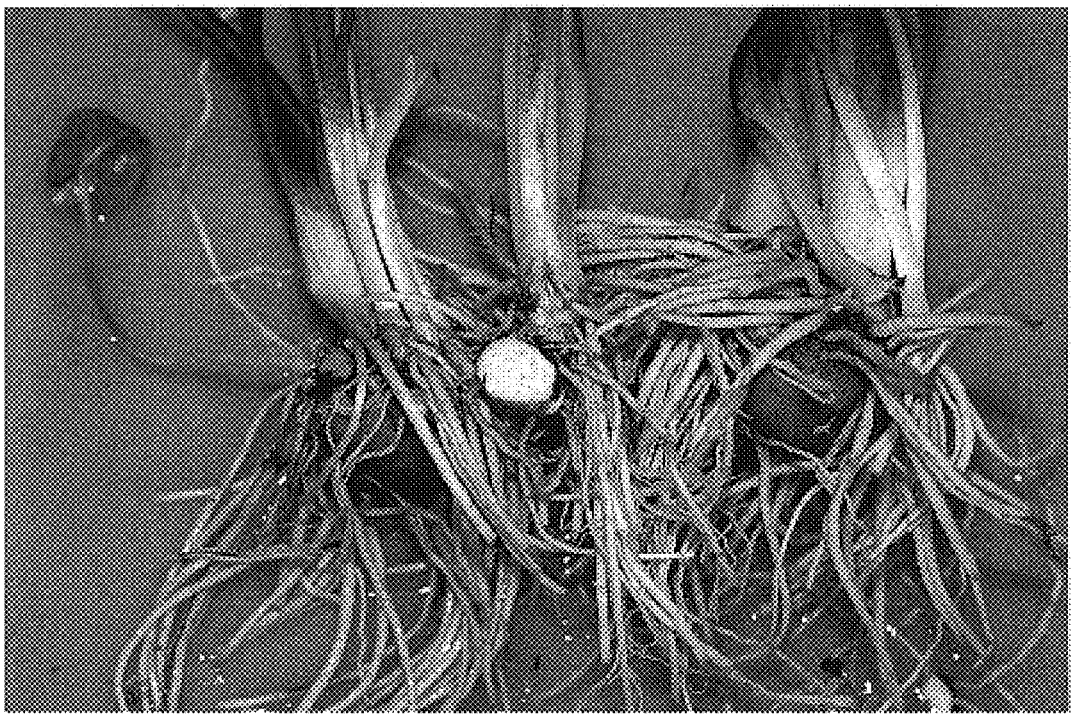

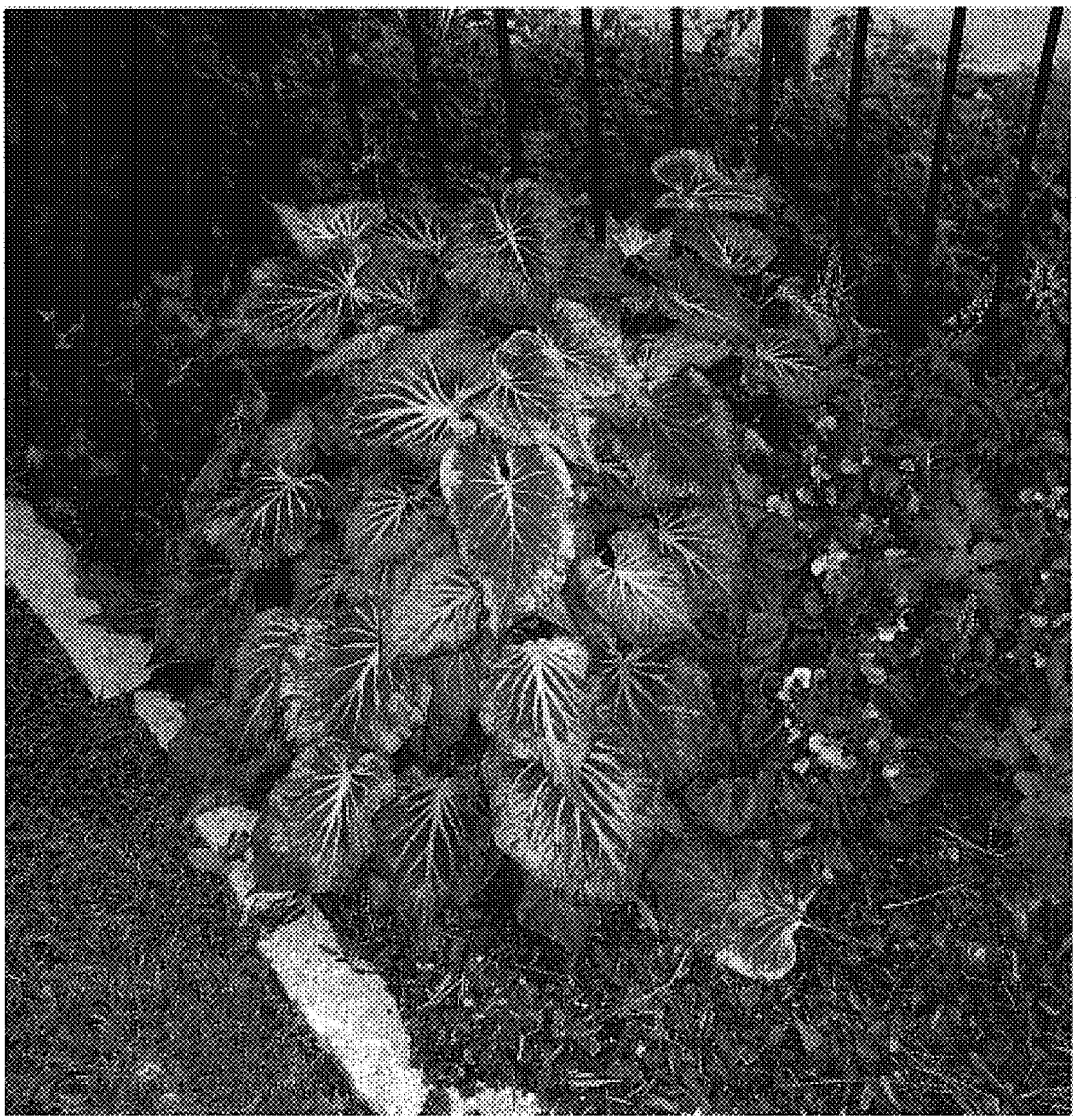

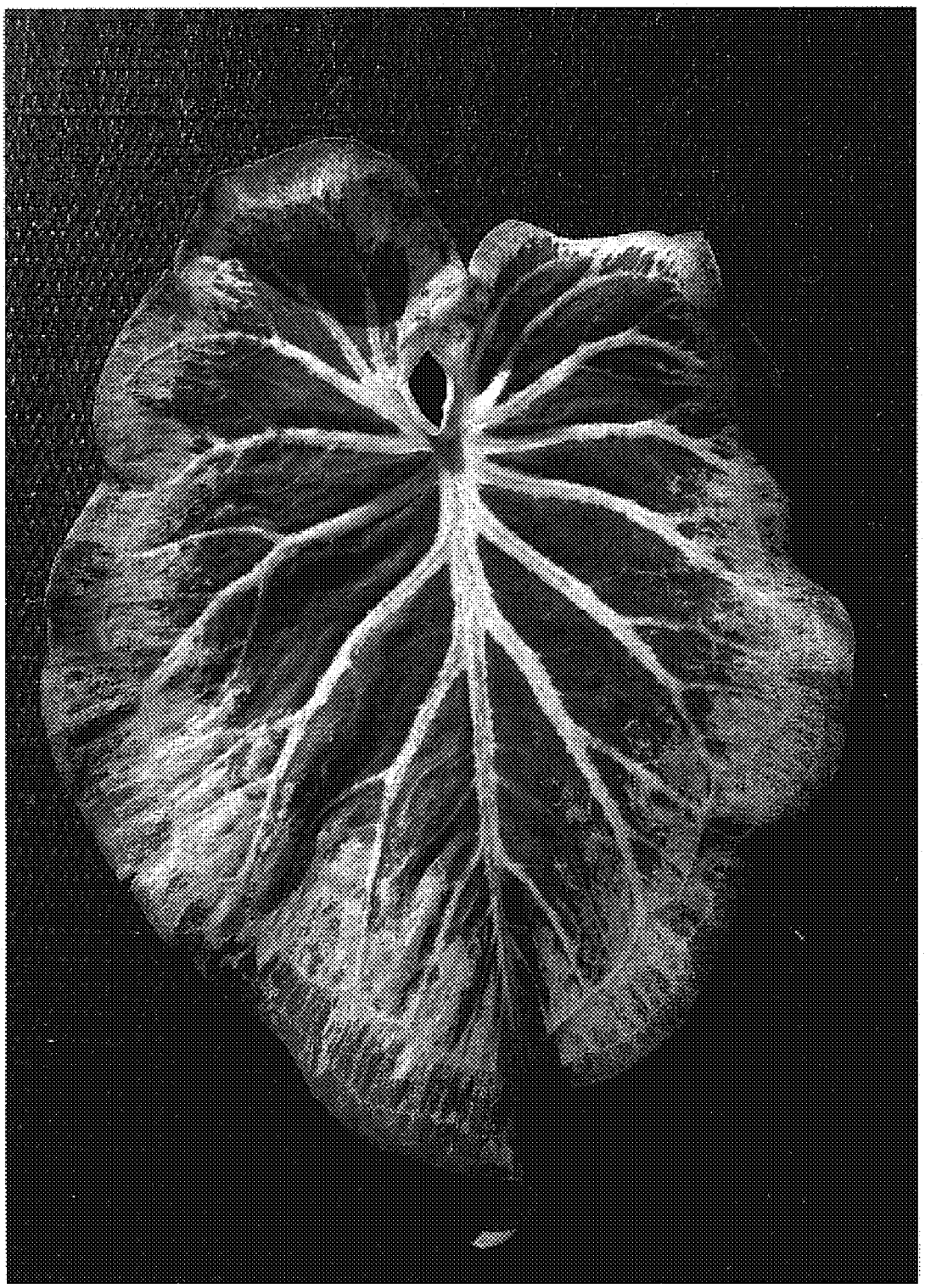

* * * * *